(12) United States Patent
Malachowski et al.

(10) Patent No.: US 9,134,220 B2
(45) Date of Patent: Sep. 15, 2015

(54) ENHANCING FLOW CYTOMETRY DISCRIMINATION WITH GEOMETRIC TRANSFORMATION

(75) Inventors: George C. Malachowski, Melbourne (AU); Paul Barclay Purcell, Ouray, CO (US); Edward Allan Stanton, Longmont, CO (US)

(73) Assignee: Beckman Coulter, Inc., Brea, CA (US)

( * ) Notice: Subject to any disclaimer, the term of this patent is extended or adjusted under 35 U.S.C. 154(b) by 2033 days.

(21) Appl. No.: 11/632,870

(22) PCT Filed: Jul. 27, 2005

(86) PCT No.: PCT/US2005/026673
§ 371 (c)(1),
(2), (4) Date: Jul. 16, 2009

(87) PCT Pub. No.: WO2006/015056
PCT Pub. Date: Feb. 9, 2006

(65) Prior Publication Data
US 2009/0287421 A1 Nov. 19, 2009

Related U.S. Application Data

(60) Provisional application No. 60/591,957, filed on Jul. 27, 2004.

(51) Int. Cl.
*G01N 33/00* (2006.01)
*G05B 21/00* (2006.01)
(Continued)

(52) U.S. Cl.
CPC ........ *G01N 15/1475* (2013.01); *G01N 33/5005* (2013.01)

(58) Field of Classification Search
CPC .............. G01N 2015/149; G01N 15/1404; G01N 15/1459; G01N 2015/1447; G01N 2015/1488; G01N 15/1427; G01N 15/1475; G01N 2015/1406; G01N 2015/1418; G01N 2015/1443; G01N 33/5005
USPC ............ 422/73; 702/21; 700/266; 435/2, 7.2, 435/40.5, 287.1; 436/63
See application file for complete search history.

(56) References Cited

U.S. PATENT DOCUMENTS 3,299,354 A 1/1967 Hogg
3,661,460 A 5/1972 Elking et al.
(Continued)

FOREIGN PATENT DOCUMENTS

DE 19549015 3/1997
EP 025296 A2 3/1981
(Continued)

OTHER PUBLICATIONS

Denk, W., et al (1995). Two-photon molecular excitation in laser scanning microscopy. Handbook of Biological Conical Microscopy. J. B. Pawley, ed., Plenum Press, New York, pp. 444-458.
(Continued)

*Primary Examiner* — Dean Kwak
(74) *Attorney, Agent, or Firm* — K&L Gates LLP; Louis C. Cullman; Andrew L. Reibman

(57) ABSTRACT

In flow cytometry, particles (2) can be distinguished between populations (8) by combining n-dimensional parameter data, which may be derived from signal data from a particle, to mathematically achieve numerical results representative of an alteration (48). An alteration may include a rotational alteration, a scaled alteration, or perhaps even a translational alteration. Alterations may enhance separation of data points which may provide real-time classification (49) of signal data corresponding to individual particles into one of at least two populations.

23 Claims, 5 Drawing Sheets

(51) Int. Cl.
*G01N 31/00* (2006.01)
*G01N 33/48* (2006.01)
*G01N 15/14* (2006.01)
*G01N 33/50* (2006.01)

(56) References Cited

U.S. PATENT DOCUMENTS

| | | |
|---|---|---|
| 3,710,933 A | 1/1973 | Fulwyler et al. |
| 3,761,941 A | 9/1973 | Robertson |
| 3,810,010 A | 5/1974 | Thom |
| 3,826,364 A | 7/1974 | Bonner et al. |
| 3,833,796 A | 9/1974 | Fetner et al. |
| 3,960,449 A | 6/1976 | Carleton et al. |
| 3,963,606 A | 6/1976 | Hogg |
| 3,973,196 A | 8/1976 | Hogg |
| 4,014,611 A | 3/1977 | Simpson et al. |
| 4,070,617 A | 1/1978 | Kachel et al. |
| 4,074,809 A | 2/1978 | McMillin et al. |
| 4,162,282 A | 7/1979 | Fulwyler et al. |
| 4,230,558 A | 10/1980 | Fulwyler |
| 4,302,166 A | 11/1981 | Fulwyler et al. |
| 4,317,520 A | 3/1982 | Lombardo et al. |
| 4,318,480 A | 3/1982 | Lombardo et al. |
| 4,318,481 A | 3/1982 | Lombardo et al. |
| 4,318,482 A | 3/1982 | Barry et al. |
| 4,318,483 A | 3/1982 | Lombardo et al. |
| 4,325,483 A | 4/1982 | Lombardo et al. |
| 4,325,706 A * | 4/1982 | Gershman et al. ........... 435/6.16 |
| 4,341,471 A | 7/1982 | Hogg et al. |
| 4,350,410 A | 9/1982 | Minott |
| 4,361,400 A | 11/1982 | Gray et al. |
| 4,395,676 A | 7/1983 | Hollinger et al. |
| 4,400,764 A | 8/1983 | Kenyon |
| 4,487,320 A | 12/1984 | Auer |
| 4,498,766 A | 2/1985 | Unterleitner |
| 4,501,336 A | 2/1985 | Kemp et al. |
| 4,515,274 A | 5/1985 | Hollinger et al. |
| 4,523,809 A | 6/1985 | Taboada et al. |
| 4,538,733 A | 9/1985 | Hoffman |
| 4,598,408 A | 7/1986 | O'Keefe |
| 4,600,302 A | 7/1986 | Sage, Jr. |
| 4,631,483 A | 12/1986 | Proni et al. |
| 4,673,288 A | 6/1987 | Thomas et al. |
| 4,691,829 A | 9/1987 | Auer |
| 4,702,598 A | 10/1987 | Bohmer |
| 4,744,090 A | 5/1988 | Freiberg |
| 4,758,729 A | 7/1988 | Monnin |
| 4,794,086 A | 12/1988 | Kasper et al. |
| 4,818,103 A | 4/1989 | Thomas et al. |
| 4,831,385 A | 5/1989 | Archer et al. |
| 4,845,025 A | 7/1989 | Lary et al. |
| 4,877,965 A | 10/1989 | Dandliker et al. |
| 4,942,305 A | 7/1990 | Sommer |
| 4,981,580 A | 1/1991 | Auer |
| 4,983,038 A | 1/1991 | Ohki et al. |
| 4,987,539 A | 1/1991 | Moore et al. |
| 5,005,981 A | 4/1991 | Schulte et al. |
| 5,007,732 A | 4/1991 | Ohki et al. |
| 5,030,002 A | 7/1991 | North, Jr. |
| 5,034,613 A | 7/1991 | Denk et al. |
| 5,079,959 A | 1/1992 | Miyake et al. |
| 5,098,657 A | 3/1992 | Blackford et al. |
| 5,101,978 A | 4/1992 | Marcus |
| 5,127,729 A | 7/1992 | Oetliker et al. |
| 5,135,759 A | 8/1992 | Johnson |
| 5,144,224 A | 9/1992 | Larsen |
| 5,150,313 A | 9/1992 | Van den Engh et al. |
| 5,159,397 A | 10/1992 | Kosaka et al. |
| 5,159,403 A | 10/1992 | Kosaka et al. |
| 5,167,926 A | 12/1992 | Kimura et al. |
| 5,180,065 A | 1/1993 | Touge et al. |
| 5,182,617 A | 1/1993 | Yoneyama et al. |
| 5,199,576 A | 4/1993 | Corio et al. |
| 5,215,376 A | 6/1993 | Schulte et al. |
| 5,247,339 A | 9/1993 | Ogino |
| 5,259,593 A | 11/1993 | Orme et al. |
| 5,260,764 A | 11/1993 | Fukuda et al. |
| 5,298,967 A | 3/1994 | Wells |
| 5,359,907 A | 11/1994 | Baker et al. |
| 5,367,474 A | 11/1994 | Auer et al. |
| 5,370,842 A | 12/1994 | Miyazaki et al. |
| 5,412,466 A | 5/1995 | Ogino |
| 5,452,054 A | 9/1995 | Dewa et al. |
| 5,466,572 A | 11/1995 | Sasaki et al. |
| 5,467,189 A | 11/1995 | Kreikebaum et al. |
| 5,471,294 A | 11/1995 | Ogino |
| 5,483,469 A | 1/1996 | Van den Engh et al. |
| 5,503,994 A | 4/1996 | Shear et al. |
| 5,523,573 A | 6/1996 | Hanninen et al. |
| 5,558,998 A | 9/1996 | Hammond et al. |
| 5,596,401 A | 1/1997 | Kusuzawa |
| 5,601,235 A | 2/1997 | Booker et al. |
| 5,602,039 A | 2/1997 | Van den Engh |
| 5,602,349 A | 2/1997 | Van den Engh |
| 5,641,457 A | 6/1997 | Vardanega et al. |
| 5,643,796 A | 7/1997 | Van den Engh et al. |
| 5,650,847 A | 7/1997 | Maltsev et al. |
| 5,672,880 A | 9/1997 | Kain |
| 5,675,401 A | 10/1997 | Wangler et al. |
| 5,700,692 A | 12/1997 | Sweet |
| 5,707,808 A | 1/1998 | Roslaniec et al. |
| 5,726,364 A | 3/1998 | Van den Engh |
| 5,759,767 A | 6/1998 | Lakowicz et al. |
| 5,777,732 A | 7/1998 | Hanninen et al. |
| 5,786,560 A | 7/1998 | Tatah et al. |
| 5,796,112 A | 8/1998 | Ichie |
| 5,815,262 A | 9/1998 | Schrof et al. |
| 5,824,269 A | 10/1998 | Kosaka et al. |
| 5,835,262 A | 11/1998 | Iketaki et al. |
| 5,880,457 A | 3/1999 | Tomiyama et al. |
| 5,885,840 A | 3/1999 | Kamensky et al. |
| 5,912,257 A | 6/1999 | Prasad et al. |
| 5,916,449 A | 6/1999 | Ellwart et al. |
| 6,248,590 B1 | 6/2001 | Malachowski |
| 6,589,792 B1 | 7/2003 | Malachowski |
| 6,630,990 B2 | 10/2003 | Van't Oever et al. |
| 6,662,117 B2 | 12/2003 | Naito |
| 6,763,149 B2 | 7/2004 | Riley et al. |
| 6,944,338 B2 | 9/2005 | Lock et al. |
| 2003/0184730 A1 | 10/2003 | Price |
| 2004/0062685 A1* | 4/2004 | Norton et al. .................. 422/81 |
| 2005/0112541 A1* | 5/2005 | Durack et al. .................. 435/2 |

FOREIGN PATENT DOCUMENTS

| | | |
|---|---|---|
| EP | 0160201 A2 | 11/1985 |
| EP | 0468100 A1 | 1/1992 |
| EP | 0781985 A2 | 7/1997 |
| EP | 0786079 B1 | 5/2003 |
| FR | 2699678 A1 | 12/1992 |
| JP | 61139747 A | 6/1986 |
| JP | 61159135 A | 7/1986 |
| JP | 2024535 | 1/1990 |
| JP | 4-126066 | 4/1992 |
| JP | 4-126081 | 4/1992 |
| JP | 4126064 A | 4/1992 |
| SU | 1056008 | 11/1983 |
| SU | 1260778 A1 | 9/1986 |
| WO | WO96/12172 | 4/1996 |
| WO | WO99/44037 | 2/1999 |
| WO | WO00/32542 | 6/2000 |
| WO | WO01/28700 | 4/2001 |

OTHER PUBLICATIONS

Garner, D. L. et al; Quantification of the X- and Y- Chromosome-Bearing Spermatozoa of Domestic Animals by Flow Cytometry.sup.1, Biology of Reproduction 28, pp. 312-321, (1983).

Goppert-Mayer, M. 1931,. Uber Elementarakte mit zwei Quantensprungen nnalen der Physik, pp. 273-294.

Johnson, Lawrence A. Sex Preselection by Flow Cytometric Separation of X and Y Chromosome-bearing Sperm based on NA Difference: a Review, Reprod. Fertil. Dev., 1995, 7, pp. 893-903.

(56) References Cited

OTHER PUBLICATIONS

Manni, Jeff; (1996). Two-Photon Excitation Expands the Capabilities of Laser-Scanning Microscopy, Biophotonics International, pp. 44-52.

Melamed et al, An Historical Review of the Development of Flow Cytometers and Sorters,, 1979, pp. 3-9.

Piston. D. W.. et al (1994). Two-photon-excitation fluorescence imaging of three-dimensional calcium ion activity. Applied Optics 33: 662-669.

Piston, D. W., et al. (1995). Three-dimensionally resolved NAD(P)H cellular metabolic redox imaging of the in-situ cornea with two-photon excitation laser scanning microscopy. J of Microscopy 178: 20-27.

Skogen-Hagenson, M. J. et al; "A High Efficiency Flow Cytometer," The Journal of Histochemistry and Cytochemistry, vol. 25, No. 7, pp. 784-789, 1977, USA.

Van Dilla et al. (Eds.)Flow Cytometry: Instrumentation and Data Analysis,, "Overview of Flow Cytometry: Instrumentation and Data Analysis" by Martin Van Dilla, 1985, pp. 1-8.

Williams, R. M. et al. (1944). Two photon molecular excitation provides intrinsic 3-dimensional resolution for laser-based microscopy and microphotochemistry. FASEB J. 8: 804-813.

McLeod, J., Eastman Kodak Company, Hawk-Eye Works, Rochester, NY, Journal of the Optical Society of America; vol. 44, No. 8, Sep. 1953, pp. 592-597.

Pinkel, D., "Flow Chambers and Sample Handling," Flow Cytometry: Instrumentation and Data Analysis, pp. 77-128 (1985).

* cited by examiner

ENHANCING FLOW CYTOMETRY DISCRIMINATION WITH GEOMETRIC TRANSFORMATION

CROSS-REFERENCES TO RELATED APPLICATIONS

This application is the United States National Stage of International Application PCT/US2005/026673, filed 27 Jul. 2005, which claims the benefit of the filing date of and right of priority to U.S. Provisional Application No. 60/591,957, filed 27 Jul. 2004, both such applications hereby incorporated by reference in their entirety.

TECHNICAL FIELD

The present invention includes in embodiments apparatus and methods for real-time discrimination of particles while being sorted by flow cytometry. Specifically, embodiments of the invention may include application of various mathematical operations to manipulate data in real-time resulting in enhanced discrimination between populations of particles.

BACKGROUND

One of the most important developments over the last few years has been the application of high speed jet-in-air sorters to discriminate particles and cells that are only subtly different. As but one example, flow cytometry can be used to separate X from Y bearing sperm. While it is in this context that some properties are discussed, it should be understood that this is only one example of a broad range of applications. Sperm sorting has been applied now to cattle, horses and pigs and may be used with various other animals. In this one application, the intent may be to obtain viable and motile sperm from semen or perhaps even be to guaranteed the sex of off-spring that are created when a sexed sperm may be inseminated into a female of a species. The requirement may be to improve animal husbandry. For example, in cattle where dairy is the main product, females may be preferred or even in beef, the male may be the desirable selection.

Subtle differences can even be quantitative, for example, sperm may not express surface antigens that are indicators of the presence of X or Y chromosomes. However, X bearing sperm may have a larger mass of genetic material. A dye, such as Hoechst, may have the property of binding to DNA. As a consequence, light emitted by X bearing sperm, when ignited by ultra-violet laser, may be slightly brighter and this can be used as a discrimination to sort and separate the sperm.

Subtle differences can also be due to flow cytometer geometries as well. In the sperm example, mammalian sperm are generally paddle shaped and when they pass through a flow cytometer they can have a random orientation. This orientation may obscure the differential light coming from the X and Y bearing cells. Consequently, a cytometer may have a specialized orienting nozzle that can use a hydrodynamic effect to orientate the cells to a reasonable degree.

A bivariate histogram may be collected, the parameters may be a forward and side angle fluorescence. A population may show the effect of orientation. A slight separation of two populations may make a drawing of a closed contour around each population difficult. A contour may be needed to establish a region that can be exclusively sorted.

DISCLOSURE OF THE INVENTION

Accordingly, it is desirable to provide enhanced discrimination between particles during flow cytometry. An object of the present invention, in embodiments, may include applying mathematical operations to data to allow enhanced discrimination between populations.

Another object of the invention in embodiments may include performing a geometric perhaps 2-dimensional transformation of flow cytometry data so that particles can be sorted.

It may be another object of the present invention to provide in embodiments an alteration of flow cytometry data in order to distinguish particles between populations. This may include rotational alterations, translation alterations, scaling alterations and the like in various embodiments.

Naturally, further objects, goals and embodiments of the inventions are disclosed throughout other areas of the specification and claims.

MODE(S) FOR CARRYING OUT THE INVENTION

The present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

Embodiments of the invention may include various methods, apparatus, systems and the like to distinguish particles during flow cytometry. A fluid stream (1) may be established in a flow cytometer in which particles (2) may be entrained. In an embodiment, particles may be sperm; however other kinds of particles are certainly possible and all are meant to be included in this disclosure. Particles may be coupled with a light emitting element, for example one embodiment may include a Hoechst dye. Each individual particle may emit a first signal and perhaps even at least one additional signal. A detector (42) may be placed so as to detect signals from the particles as can be understood from FIGS. 1 and 2. In embodiments, a first signal detector may detect a first signal affiliated with an individual particle and perhaps even at least one additional signal detector may detect at least one additional signal affiliated with an individual particle. This may include any kind of signal that may be in association, perhaps even close association with an individual particle such as but not limited to fluorescence, radiance, and the like.

Figure 1:
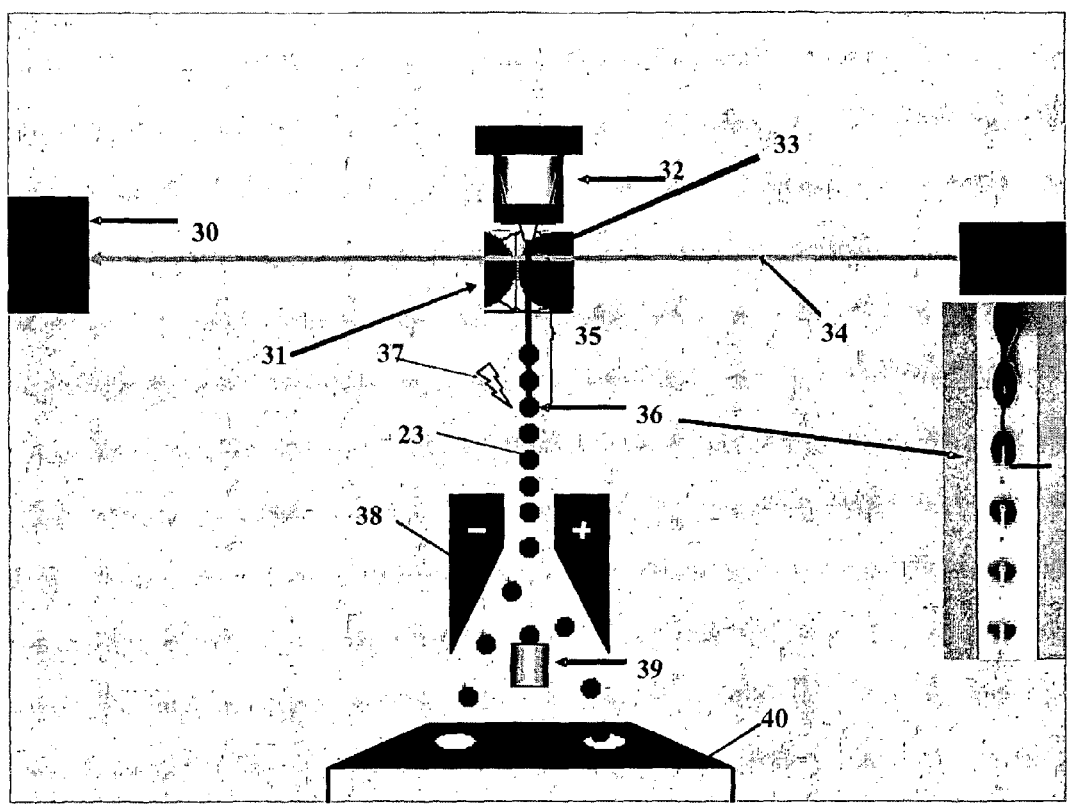
FIG. 1 is an illustration of a sort overview in accordance with some embodiments of the present invention.
Figure 2:
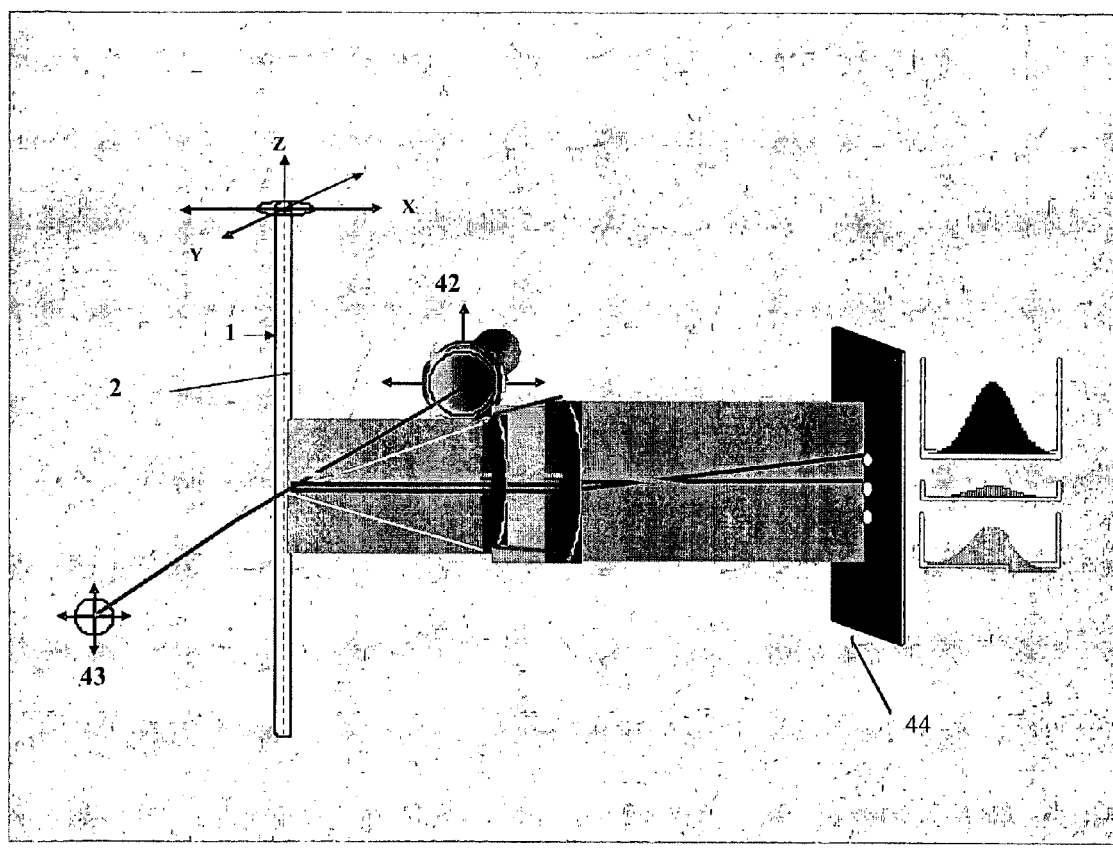
FIG. 2 illustrates forward and side light detection systems in accordance with some embodiments of the present invention.

As an example, FIGS. 1 and 2 represent a flow cytometry sort overview. A nozzle (32) may allow particles (2) entrained in a fluid stream (1) to move through a laser beam (34) at an interrogation point (33). A signal detector (42) such as a forward scatter detector (30) and perhaps even a side scatter collection objective (31) may be placed appropriately to collect signals affiliated to a particle. It may also be desirable to provide primary laser focusing optics (43). In embodiments, signals may include fluorescence emitted from a light emitting particle coupled with individual particles after passing through a laser beam. Signals emitted from a particle may be passed through optics and perhaps even a pinhole strip (44) to assist in collection of data. A signal detector may be connected to a system, as discussed hereafter, in which signal data indicative of the signals may be processed and analyzed in order to determine a sort decision. Computers, computer programming, hardware, software and the like may assist in a sort decision. While a sort decision is being determined, particles may pass through a drop delay (35). This time frame may be very short. After a sort decision may have been made, a pulse of charge (37) may be applied to a droplet (23) containing a particle. Droplets may pass through charged deflection plates (38) in order to sort particles into a desired sort receptacle (40) having containers. A waste collection tube (39) may be included in embodiments.

In order to distinguish particles, signal data may be analyzed. Embodiments may include converting signals (e.g. a first signal and at least one additional signal) affiliated with each individual particle into n-dimensional parameter data. This may be done with a signal processor responsive to the signals. A signal processor may provide a conversion of a first signal and at least one additional signal into n-dimensional parameter data. N-dimensional parameter data may include one-dimensional or perhaps even multi-dimensional (2-D, 3-D, 4-D, etc.) data which can be associated with each signal detected. Signal data may be converted to relate each signal with a coordinate, such as an intensity of a color, and the like and may even be plotted in a Cartesian coordinate system.

Signals, perhaps even n-dimensional data, may be plotted on a graph (13). Since differences between particles may vary slightly, signals affiliated with the particles may also vary slightly. This slight difference may be so small that when plotted, the n-dimensional parameter data corresponding to the signals, may place data points very close together. These may be so close that it may be difficult to categorize the data points into a population. Conventional technologies may have disregarded these points that are so close together and may have decided to throw out that particle because it could not have been distinguished. It may be desirable in embodiments to reconfigure data to enhance separation between data points.

Embodiments may include distinguishing at least two populations (8) of n-dimensional parameter data. A population differentiation element may include a geometric transformation and may allow n-dimensional parameter data to be categorized into one of at least two populations. For example, a sperm may be categorized into a X-bearing sperm population and a Y-bearing population. A geometric two-dimensional transformation may be performed on flow cytometry data such that particles or even cells may be sorted into separate vials based on an appropriate property. In the sperm example, one vial containing cells for male and one vial containing cells for female. A transformation may include a matrix dot product of various translation, scale, and perhaps even rotation operations for discriminating male determining from female determining cells and may even maintain proper cell type identification during signal drift over time. The transformations may be combined into a single transformation matrix so that the calculations can be performed within the available signal processing time such as with a Digital Signal Processor.

In embodiments, the present invention may include real-time classifying n-dimensional parameter data of each of the individual particles into one of at least two populations. A real-time classification element may include classifying signal data into a population, making a sort decision, and sorting a particle all within the small amount of time it takes for the particle to move through a flow cytometer. Accordingly, the present invention may provide in embodiments, sorting individual particles based upon a real-time classification.

Figure 3:
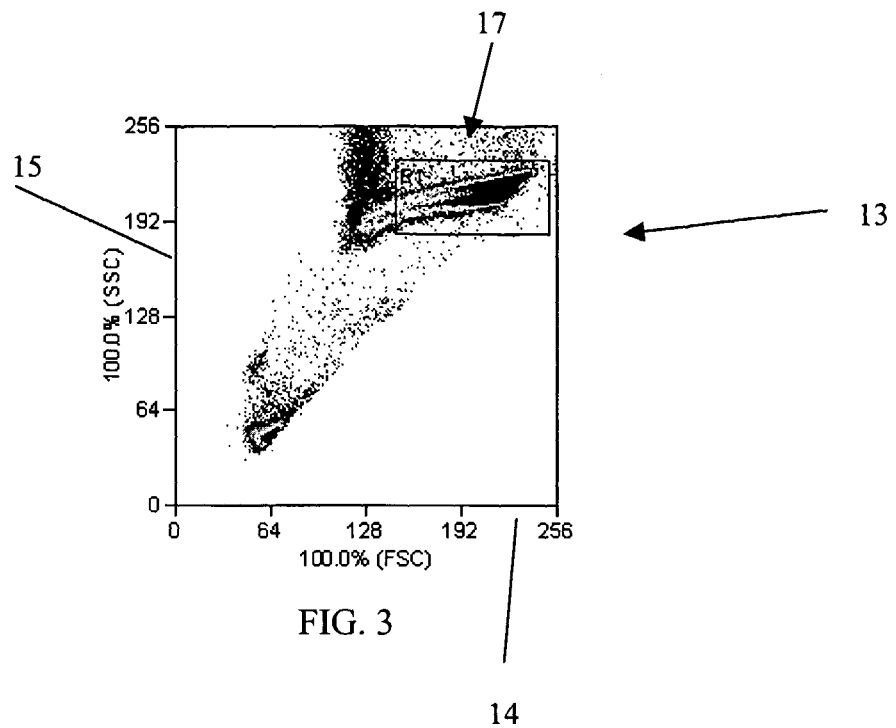
FIG. 3 is an example of a histogram of sperm sorting data prior to rotation.

The present invention may provide in embodiments, visually distinguishing at least two populations of n-dimensional parameter data. This may assist a user to ensure that a sorting may be running properly. This may also allow for user input to assist in discrimination between populations. Embodiments may include graphically placing n-dimensional parameter data for each of the individual particles in relation to at least two populations. For example, it may be desirable to plot n-parameter data in a Cartesian coordinate system. A first signal may be plotted on one axis (14) and at least one additional signal may be plotted on at least one additional axis (15), as can be seen in FIG. 3. In yet other embodiments, a histogram (17) of the n-dimensional parameter data may be provided.

Certain particles or cells may exhibit signals that can show enhanced differences by translation or scaling effects. For example, a male determining and female determining sperm cell may not be discriminated from each other using a typical unaltered light signal detected by a flow cytometer. Although a digitized signal may have 12 bits of resolution, a sorting electronics may have 8 bits of resolution possibly discarding the lower 4 bits. A detected light from male determining and female determining sperm cells may be so similar that the lower 4 bits may be required to discriminate between them. Likewise, due to their similarity, the cells may not effectively be discriminated in histogram data analysis of the detected parameters possibly because histograms may also degrade resolution.

Particles or sperm cells may occupy a small area of a histogram (17). The variation of detected signals of cells or particles, perhaps such as male determining sperm cells with respect to female determining sperm cells may be small; as may be the variation within cell or particles of the same type. The total range of variation for both types of cells or particles may span less than half the total available range. Therefore, the lower bits of resolution may be important for discriminating between the cells or particles and perhaps even the upper bits may not be necessary to identify both types of cells or particles. The invention may exploit this characteristic, in embodiments, by translating a center of the total range of signal variation for both types of cells or particles to an origin of a Cartesian coordinate system, scaling the data about the origin effectively increasing the variance between types, then translating back to its original location. As a result, histogram data may show sufficient variation for discriminating between two types of cells or particles while even preserving enough information to identify both types from instrument noise, dead or destroyed cells, other foreign particles, and the like. This has particular applicability for sperm cell sex discrimination.

N-dimensional parameter data may be combined, in embodiments, to mathematically achieve numerical results representative of an alteration. An alteration calculation may include any kind of manipulation of data. For example, embodiments may provide manipulating n-dimensional parameter data mathematically to achieve a desired result. This may include a rotational alteration perhaps with a rotational alteration calculation applied to n-dimensional parameter data. Other embodiments may include a translation alteration perhaps with a translational alteration calculation. In yet other embodiments, n-dimensional parameter data may be combined to mathematically achieve numerical results representative of a scaling operation perhaps with a scaled alteration calculation. Of course, other kinds of alterations and calculations may be used and any alteration may be applied as a single operation or perhaps even in combination with others. Classification of a particle may be based upon numerical results representative of an alteration.

Figure 7:
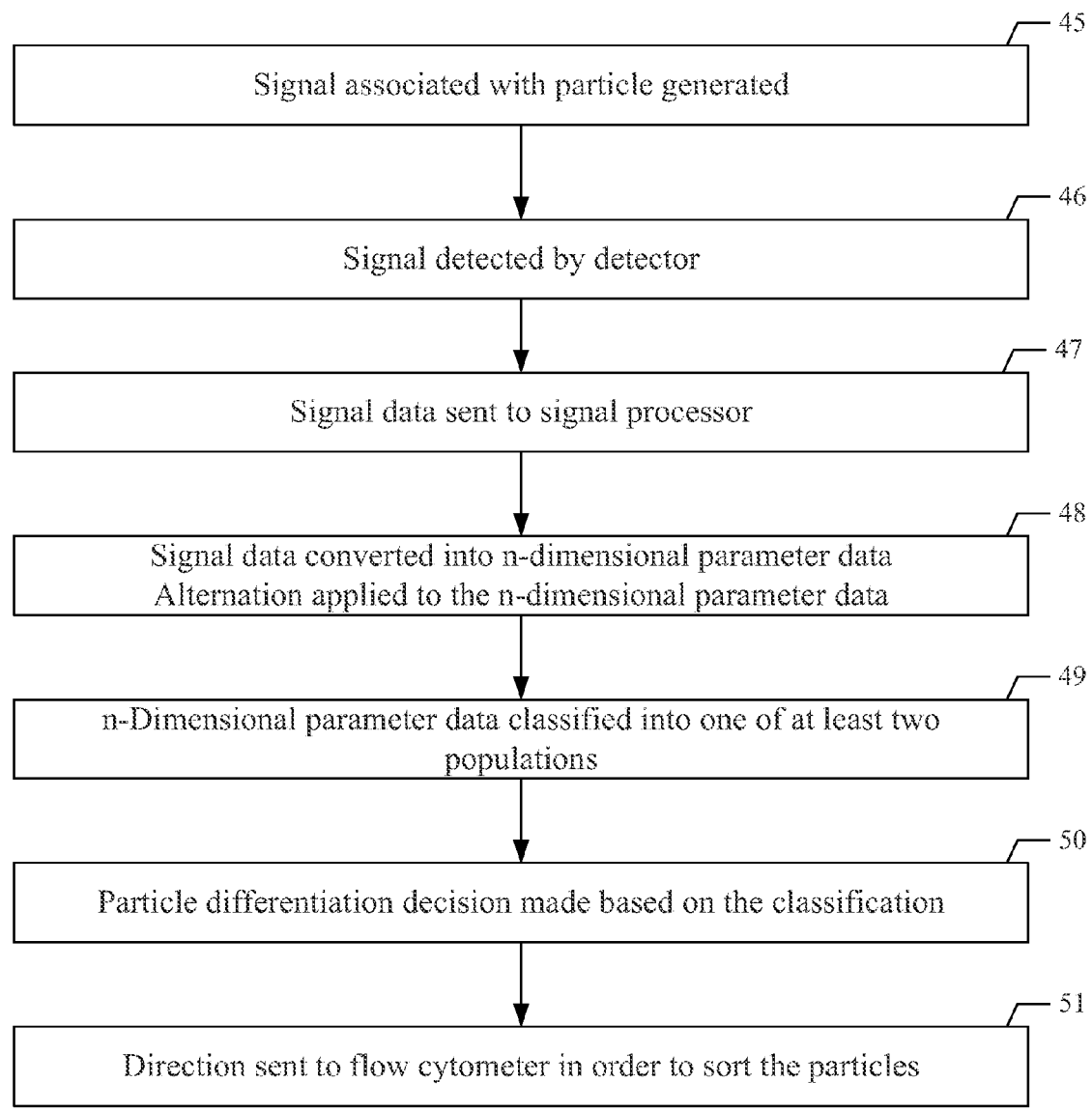
FIG. 7 is a conceptual depiction of a system for analyzing detected signal data in one embodiment.

In embodiments, and as can be conceptually understood from FIG. 7, a signal (45) associated with a particle may be detected by at least one detector (46) in which signal data may be sent to a signal processor (47). In a signal processor, signal data may be converted into n-dimensional parameter data to which at least one alteration (48) (e.g. rotational alteration, translation operation, scaling operation, any combination of these and the like) may be applied to the n-dimensional parameter data. Based on the alteration, n-dimensional parameter data may be classified into one of at least two populations providing a real-time classification (49). A particle differentiation decision (50) may be made based upon a real-time classification of the n-dimensional parameter data to which directions may be sent to a flow cytometer (51) in order to charge and sort the particles.

Certain particles or cells may exhibit signals that can show enhanced differences by a rotational alteration of the data. For example, in embodiments, the invention may involve rotating data to increase a separation of data from male determining cells to female determining cells. Two sources of light may be detected for each cell. The range of light intensity from one source from male determining cells may overlap the same light source range from female determining cells. Employing a scale factor, as described above, may increase the separation of the mean distribution of the signal range but may not completely eliminate an overlap.

To eliminate the overlap in this particular example, the invention may consider a shape of the signal distribution in two-dimensional analysis where signals from perhaps both light sources may be correlated in a two-dimensional Cartesian coordinate system. Graphically, each of the populations such as cell types may have an elliptical shaped population (18) with similar non-orthogonal angles of inclination of a major axis and may even have a similar length of a minor axis. The difference in Y-intercept of the ellipse major axis for one cell type to the other type may be greater than the length of the minor axis. Since the major axes may be nearly parallel, it may be desirable to orient the elliptical shaped populations orthogonal to at least one axis. A rotation about a mid-point between the two major axes may orient each ellipse orthogonal to the Y-axis possibly effectively eliminating the Y-axis overlap.

Signals such as perhaps light intensity may vary with time, which may preclude the setting of fixed regions by which sort decisions may be based. During a long sort, populations may drift due to physical changes to the detectors, absorption or degradation of dye, and even other uncontrollable conditions. Consequently, sort regions may need to be monitored and adjusted during the sort. This may be tedious, labor intensive and even prone to error.

One embodiment of the present invention may hold a population in its original location by employing a scale operation in the transformation matrix. One possible scale factor could be a ratio of an initial mean value of the signal range with respect to the current mean; which may effectively scale the signal up or down proportionately to the amount of drift from the initial mean.

As previously mentioned, a flow cytometer may be used to generate a stream into which the cells or other particulates may be injected. A detection point may be established which may cause a source of laser light to strike the cells perhaps causing a dye that is carried on genomic material to fluoresce. In one application, sperm may be orientated by the hydrodynamics of the injection device, and perhaps the fluorescence level could be proportional to the amount of genomic mass. Thus, a differential between X and Y bearing sperm can be detectable. Fluorescence may be detected by sensors established forward of the detection point and possibly even to an angle, such as 90 degrees, of this point as may be understood in FIGS. 1 and 2. A sensory system can pass a pulse of light to an electrical device which may convert a pulse level into binary numbers suitable for manipulation by a Digital Signal Processor ("DSP").

A signal processor, for example a Digital Signal Processor may contain highly optimized algorithms that can perform a specialization transformation of at least two signal values. This transformation may cause a resulting population of signal to adopt a form, such as where a separation of X and Y bearing sperm may be delineated. Clarity of delineation may allow each population to be selected more accurately than in any other separation system.

The selection of which population is to be sorted can be made by an electronic system such as by controlling a droplet break-off of a standard flow cytometer. There may be a delay between a detection of a fluorescence and a particle falling into a last breaking drop (36). This time may be known. Thus an electronic system can apply an electric charge to the drop containing the particle of interest. High voltage plates below the breaking drops may cause the drop to move and be placed into a collection vial. In this fashion, a high level of selected particles, perhaps such as pure sperm cells can be collected as may be understood in FIG. 1.

A Digital Signal Processor may control the position of the populations. Flow cytometers may have variability in the pointing accuracy of a laser beam which can cause an intensity of fluorescence from each cell to shift. A DSP may act as a sensory device to monitor a shifting of light intensity and may even perform a correcting scale to ensure that the populations residing in the fluorescence bivariate remain in the same position. This may ensure that the correct sperm are sorted. The process of transformation, zooming and perhaps even control may be imbedded in one geometric transform. Multiple transformation and zoom could be incorporated perhaps even with non-linear, logarithmic, table look up, or even discretely unique data portion transformations. Transformation may uniquely supply the accuracy required to provide highly pure particle separation.

One method of gaining spatially separated data may be to use compensation algorithms as those skilled in the art could appreciate. Rotation of the data (forward scatter vs. side scatter) may be a more accurate mechanism to do this. In addition to rotation, it has been found that there may be a need for tracking and zooming of the data. These combinations can be significant, for example sex selection may not be optimally achieved by any other method, hence the importance of this invention.

By rotating a bivariate histogram in which two populations may be present but overlapping in one dimension, a better spatial separation in the dimension that is overlapped may be created. Rotated data can be used as a parameter in sort decisions and perhaps even in any other histograms. If data has been properly rotated, a univariate histogram of the parameter of interest can contain gaps in the populations. In embodiments, a rotation function may be utilized to set the X and Y populations on a bivariate to be horizontal.

Because the populations of interest may typically be close together, it may be desirable—either alone or in combination with other aspects—to zoom in on a region in order to exaggerate a distinction between the populations. This may be another mechanism to allow separation of the populations. Further, the long sorts typical of sperm sorting or the like may cause data to shift over time. Shifts may be fixed by setting a tracking region and using this region in a newly computed parameter. In embodiments, an automatic region setting algorithm may be implemented. In other embodiments, regions may be set according to a desired purity level.

In order to rotate and sort data, a rotation could be done using hardware that can access the data in an acquisition rack and may have a capability to modify an event frame prior to a sort decision being made. Rather than design new hardware, it may be desirable to implement this in a DSP perhaps by using a rotation algorithm. This may include an ability to do compensation on data when rotating it. In addition to rotation, a user can specify a region to zoom in on.

In embodiments, the present invention may provide specification of a center point of a rotation. This may allow a finer control of the rotation in order to achieve maximum separation.

Embodiments of the present invention may include providing a n-dimensional space alteration function having at least:
a first 1st-dimensional alteration value, a second 1st-dimensional alteration value, and a third 1st-dimensional alteration value;
a first 2nd-dimensional alteration value, a second 2nd-dimensional alteration value, and a third 2nd-dimensional alteration value, and the like.
This may be representative of a matrix, as one skilled in the art can appreciate and can be understood by the various examples given herein.

N-dimensional space alteration functions may be combined with a vector having data points so as to alter the n-dimensional parameter data. In an embodiment, a combination of a function and data points may include, but is not limited to: calculating a first 1st-dimensional alteration value times a 1st-dimensional data point summed with a second 1st-dimensional alteration value times a 2nd-dimensional data point summed with a third 1st-dimensional alteration value times a 3rd-dimensional data point to thereby create a first dimensional altered data point; and calculating a first 2nd-dimensional alteration value times a 1st-dimensional data point summed with a second 2nd-dimensional rotational value times a 2nd-dimensional data point summed with a third 2nd-dimensional alteration value times a 3rd-dimensional data point to thereby create a second dimensional altered data point.

In other embodiments, a n-dimensional space alteration function may include a first 3rd-dimensional alteration value, a second 3rd-dimensional alteration value and a third 3rd-dimensional alteration value. Further, a combination of data may include calculating a first 3rd-dimensional alteration value times a 1st-dimensional data point summed with a second 3rd-dimensional rotational value times a 2nd-dimensional data point summed with a third 3rd-dimensional alteration value times a 3rd-dimensional data point to thereby create a third dimensional altered data point.

Many different types of data manipulation values that may be used as an alteration value. For example, a rotational alteration may include alteration values based upon an angle of rotation allowing altered data points to increase discrimination of at least two populations of n-dimensional data. In other embodiments, a scaled alteration may include alteration values are based upon a zoom and tracking element allowing altered data points to increase discrimination of at least two populations of n-dimensional data. In yet other embodiments, a translation alteration may include alteration values which may translate n-parameter data with respect to a center point of rotation.

The following are examples of matrices that may be used in order to do rotation about a given center point and even zoom or tracking on a region and the like.

Translate data:

$$T(C_x, C_y) = \begin{pmatrix} 1 & 0 & Cx \\ 0 & 1 & Cy \\ 0 & 0 & 1 \end{pmatrix}$$

Rotate the data:

$$R\theta = \begin{pmatrix} \cos\theta & \sin\theta & 0 \\ -\sin\theta & \cos\theta & 0 \\ 0 & 0 & 1 \end{pmatrix}$$

Scale the data (Zoom and Tracking):

$$S(D_x, D_y) = \begin{pmatrix} Dx & 0 & 0 \\ 0 & Dy & 0 \\ 0 & 0 & 1 \end{pmatrix}$$

These can be combined with the variables:
Res=Resolution/2
Z=Zoom amount
RC=Rotation Center
Tr=Tracking constant
ZC=Tracking center
Θ=Angle of rotation
into a single transformation produced by the product of any or all of the following linear operations:
T($Res_x$, $Res_y$)
S($Z_x$, $Z_y$)
T($-ZC_x$, $-ZC_y$)
S($Tr_x$, $Tr_y$)
T($RC_x$, $RC_y$)
Rθ
T($-RC_x$, $-RC_y$)

The equation, T($-RC_x$, $-RC_y$), may translate an event to an origin and then the opposite in order to translate it back to a proper coordinate system. This may be done with all listmode data in the first quadrant.

When zooming, the data that is being zoomed may be centered in a histogram. This may be why that data could be translated to half (½) the resolution rather than back to a center point of a zoomed region.

Other examples of translation alterations may be based upon an operation such as rotation in x-axis, rotation in y-axis, rotation in z-axis, translation, scale, perspective, higher order and the like operations. Some examples include the following 3-D algorithms:

Rotation in X-Axis:

$$R_X(\theta) = \begin{vmatrix} 1 & 0 & 0 & 0 \\ 0 & \cos(\theta) & -\sin(\theta) & 0 \\ 0 & \sin(\theta) & \cos(\theta) & 0 \\ 0 & 0 & 0 & 1 \end{vmatrix}$$

Rotation in Y-Axis:

$$R_Y(\theta) = \begin{vmatrix} \cos(\theta) & 0 & \sin(\theta) & 0 \\ 0 & 1 & 0 & 0 \\ -\sin(\theta) & 0 & \cos(\theta) & 0 \\ 0 & 0 & 0 & 1 \end{vmatrix}$$

Rotation in Z-Axis:

$$R_Z(\theta) = \begin{vmatrix} \cos(\theta) & -\sin(\theta) & 0 & 0 \\ \sin(\theta) & \cos(\theta) & 0 & 0 \\ 0 & 0 & 1 & 0 \\ 0 & 0 & 0 & 1 \end{vmatrix}$$

Translation:

$$T(T_X, T_Y, T_Z) = \begin{vmatrix} 1 & 0 & 0 & T_X \\ 0 & 1 & 0 & T_Y \\ 0 & 0 & 1 & T_Z \\ 0 & 0 & 0 & 1 \end{vmatrix}$$

Scale:

$$S(S_X, S_Y, S_Z) = \begin{vmatrix} S_X & 0 & 0 & 0 \\ 0 & S_Y & 0 & 0 \\ 0 & 0 & S_Z & 0 \\ 0 & 0 & 0 & 1 \end{vmatrix}$$

Of course other algorithms may be used and all are meant to be included in this disclosure. The examples provided herein are not meant to be limiting.

Programs may solve the particular equation used and may download the result to the DSP. A DSP code may perform a simple matrix multiplication using the matrices supplied by computer programs. Further, a computer program may create zoom parameters such that a mean of the zoomed signals may remain fixed. The mean may remain at the same position within a tracking region. Software may allow a user to designate regions bounds which a zoom function may utilize. Software may send a center of a zoom, zoom value and even tracking gain to a DSP.

In embodiments, zooming of a square region on a split of populations (such as X and Y populations) may be shown on a Forward-Fluorescence versus a Side-fluorescence bivariate histogram. A zoom region may be a square or perhaps even non-square with a maximum size which may be equal to a size of a bivariate. In embodiments, it may be desirable to use a gain set at 1 and offset at 0 on both parameters. A zoom region can be set as a fraction in percentage of the bivariate range in linear units. As those skilled in the art would recognize, 1/16 may offer a digital advantage. In embodiments, software gain (distinct from a zoom gain) can be altered. Because the DSP may be a fixed point processor, a highly optimized assembly code may be used to do the floating point math.

In order to achieve efficient calculations of data within the sort time period of real time classifying, the present invention in embodiments may include simultaneously processing two or more alteration calculations. This may include simultaneously processing n-dimensional parameter data to mathematically achieve numerical results of both a rotational alteration and a scaled alteration. Other embodiments may include simultaneously processing n-dimensional parameter data to mathematically achieve numerical results of a rotational alteration, a scaled alteration and perhaps even a translation alteration. Of course, additional alterations may be simultaneously or perhaps even sequentially processed as well.

Figure 4:
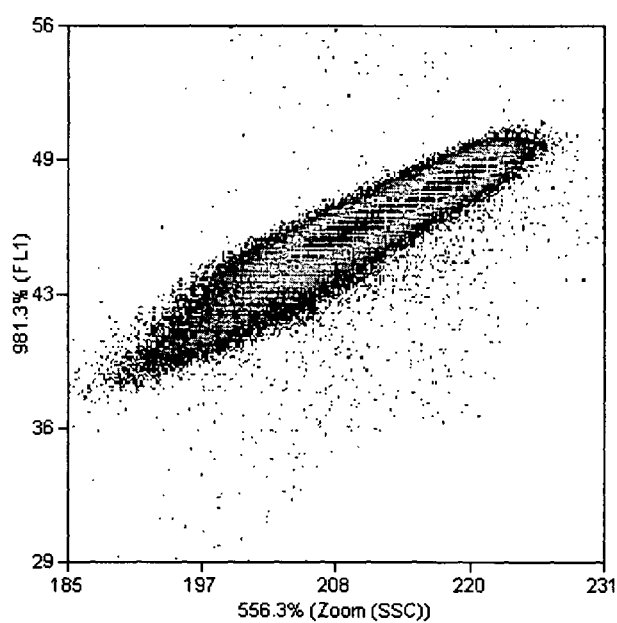
FIG. 4 is an example of a histogram of sperm sorting data after scaling.
Figure 5:
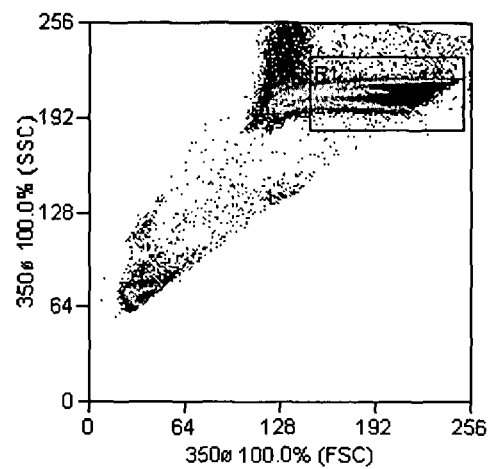
FIG. 5 is an example of a histogram of sperm sorting data after rotation.
Figure 6:
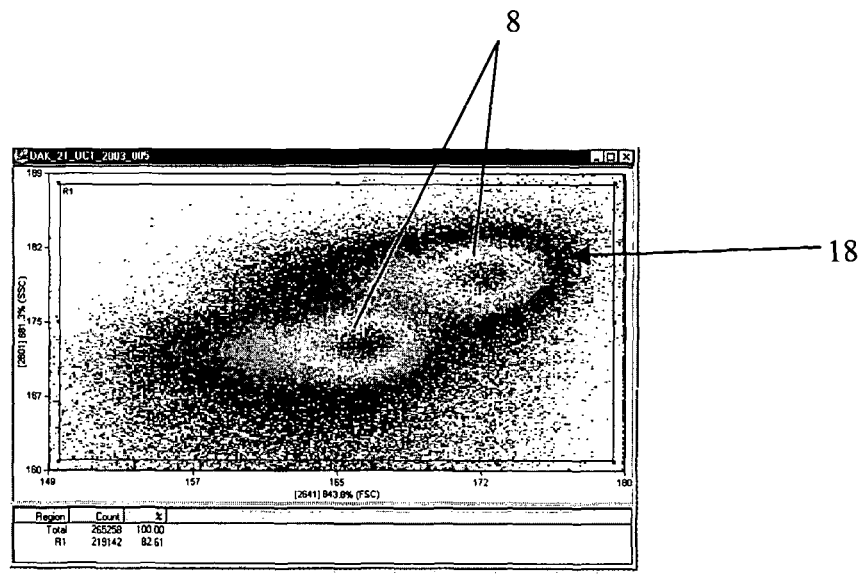
FIG. 6 is an example of a histogram of sperm sorting data after scaling and rotation.

FIG. 3 may be an image of data prior to rotation. FIG. 4 shows an image of data after scaling, FIG. 5 show an image of data after rotation and FIG. 6 shows an image of data after scaling and rotation. These may include one type of illustrations of data that can be expected. It is also common to see these illustrations of data from sperm sorting data. While rotating may allow a user to gain spatially separated data, it may distort the relative values of intensity and in embodiments, may not be used for any reason other than gaining the space between distinct populations. It may be possible to remove the values on the axis of the rotated data in order to assure that users have a visual way of recognizing this.

As can be easily understood from the foregoing, the basic concepts of the present invention may be embodied in a variety of ways. It involves both transformation techniques as well as devices to accomplish the appropriate transformation. In this application, the transformation techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "detector" should be understood to encompass disclosure of the act of "detecting"—whether explicitly discussed or not—and, conversely, were there effectively disclosure of the act of "detecting", such a disclosure should be understood to encompass disclosure of a "detector" and even a "means for detecting." Such changes and alternative terms are to be understood to be explicitly included in the description.

Any patents, publications, or other references mentioned in this application for patent are hereby incorporated by reference. All priority cases are also incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of references below or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

| I. U.S. PATENT DOCUMENTS | | |
| --- | --- | --- |
| DOCUMENT NO. & KIND CODE (if known) | PUB'N DATE mm-dd-yyyy | PATENTEE OR APPLICANT NAME |
| 3,299,354 | 12/17/67 | Hogg |
| 3,661,460 | 05/09/72 | Elking et al. |
| 3,710,933 | 01/16/73 | Fulwyler et al |
| 3,761,941 | 09/25/73 | Robertson |
| 3,810,010 | 05/07/74 | Thom |
| 3,826,364 | 07/30/74 | Bonner et al |
| 3,833,796 | 11/03/74 | Fetner et al |
| 3,960,449 | 07/01/76 | Carleton et al |
| 3,963,606 | 06/15/76 | Hogg |
| 3,973,196 | 08/03/76 | Hogg |
| 4,014,611 | 03/29/77 | Simpson et al |
| 4,070,617 | 01/24/78 | Kachel et al |
| 4,074,809 | 2/21/2978 | McMillin et al. |
| 4,162,282 | 07/24/79 | Fulwyler et al |
| 4,230,558 | 10/28/80 | Fulwyler |
| 4,302,166 | 11/24/81 | Fulwyler et al |
| 4,317,520 | 03/02/82 | Lombardo et al |
| 4,318,480 | 03/09/82 | Lombardo et al |
| 4,318,481 | 03/09/82 | Lombardo et al |
| 4,318,482 | 03/09/82 | Barry et al |
| 4,318,483 | 03/09/82 | Lombardo et al |
| 4,325,483 | 04/20/82 | Lombardo et al |
| 4,341,471 | 07/27/82 | Hogg et al |
| 4,350,410 | 09/21/82 | Minott |
| 4,361,400 | 11/30/82 | Gray et al |
| 4,395,676 | 07/26/83 | Hollinger et al |
| 4,400,764 | 08/23/83 | Kenyon |
| 4,487,320 | 12/11/84 | Auer |
| 4,498,766 | 02/12/85 | Unterleitner |
| 4,501,336 | 02/26/1985 | Kemp et al. |
| 4,515,274 | 05/07/85 | Hollinger et al |
| 4,523,809 | 06/18/85 | Toboada et al |
| 4,538,733 | 11/03/85 | Hoffman |
| 4,598,408 | 07/01/86 | O'Keefe |
| 4,600,302 | 07/15/86 | Sage, Jr. |
| 4,631,483 | 12/23/86 | Proni et al |
| 4,673,288 | 06/16/87 | Thomas et al |
| 4,691,829 | 09/08/87 | Auer |
| 4,702,598 | 10/27/87 | Böhmer |
| 4,744,090 | 05/10/88 | Freiberg |
| 4,758,729 | 07/19/88 | Monnin |
| 4,794,086 | 01/27/88 | Kasper et al |
| 4,818,103 | 04/04/89 | Thomas et al |
| 4,831,385 | 05/16/89 | Archer et al |
| 4,845,025 | 07/04/89 | Lary et al |
| 4,877,965 | 10/31/89 | Dandliker et al |
| 4,942,305 | 07/17/90 | Sommer |
| 4,981,580 | 01/01/91 | Auer |
| 4,983,038 | 01/08/91 | Ohki et al |
| 4,987,539 | 01/22/91 | Moore, et al. |
| 5,005,981 | 04/09/91 | Schulte et al |
| 5,007,732 | 04/16/91 | Ohki et al |
| 5,030,002 | 07/09/91 | North, Jr. |
| 5,034,613 | 07/23/91 | Denk et al |
| 5,079,959 | 01/14/92 | Miyake et al |
| 5,098,657 | 03/24/92 | Blackford et al |
| 5,101,978 | 04/07/92 | Marcus |
| 5,199,576 | 04/06/93 | Corio, et al. |
| 5,127,729 | 07/07/92 | Oetliker et al |
| 5,135,759 | 08/04/1992 | Johnson |
| 5,144,224 | 09/01/92 | Larsen |
| 5,150,313 | 09/22/92 | Van den Engh et al |
| 5,159,397 | 10/27/92 | Kosaka et al |
| 5,159,403 | 10/27/92 | Kosaka |
| 5,167,926 | 12/01/92 | Kimura et al |
| 5,180,065 | 01/19/93 | Touge et al |
| 5,182,617 | 01/26/93 | Yoneyama et al |
| 5,199,576 | 04/06/93 | Corio et al |
| 5,215,376 | 06/01/93 | Schulte et al |
| 5,247,339 | 09/21/93 | Ogino |
| 5,259,593 | 11/09/93 | Orme et al |

I. U.S. PATENT DOCUMENTS

| DOCUMENT NO. & KIND CODE (if known) | PUB'N DATE mm-dd-yyyy | PATENTEE OR APPLICANT NAME |
|---|---|---|
| 5,260,764 | 11/09/93 | Fukuda et al |
| 5,298,967 | 03/29/94 | Wells |
| 5,359,907 | 11/01/94 | Baker et al |
| 5,367,474 | 11/22/94 | Auer, et al. |
| 5,370,842 | 12/06/94 | Miyazaki et al |
| 5,412,466 | 05/02/95 | Ogino |
| 5,452,054 | 09/19/95 | Dewa et al |
| 5,466,572 | 11/14/95 | Sasaki, et al |
| 5,467,189 | 11/14/95 | Kreikebaum et al |
| 5,471,294 | 11/28/1995 | Ogino |
| 5,483,469 | 01/09/96 | Van den Engh et al |
| 5,503,994 | 04/02/1996 | Shear et al. |
| 5,523,573 | 06-04-96 | Hänninen et al |
| 5,558,998 | 09/24/96 | Hammond, et al |
| 5,596,401 | 01/21/97 | Kusuzawa |
| 5,601,235 | 02/11/97 | Booker et al |
| 5,602,039 | 02/11/97 | Van den Engh |
| 5,602,349 | 02/11/97 | Van den Engh |
| 5,641,457 | 07/24/97 | Vardanega, et al |
| 5,643,796 | 07/01/97 | Van den Engh et al |
| 5,650,847 | 07/22/97 | Maltsev et al |
| 5,672,880 | 09/30/97 | Kain |
| 5,675,401 | 10/07/97 | Wangler et al |
| 5,700,692 | 12/23/97 | Sweet |
| 5,707,808 | 01/13/98 | Roslaniec et al |
| 5,726,364 | 03/10/98 | Van Den Engh |
| 5,759,767 | 06/02/98 | Lakowicz et al |
| 5,777,732 | 06/07/98 | Hanninen et al |
| 5,786,560 | 07/28/98 | Tatah et al |
| 5,796,112 | 08/18/98 | Ichie |
| 5,815,262 | 09/29/98 | Schrof et al |
| 5,824,269 | 10/20/1998 | Kosaka et al. |
| 5,835,262 | 11/10/98 | Iketaki et al |
| 5,880,457 | 03/09/1999 | Tomiyama et al. |
| 5,912,257 | 06/15/99 | Prasad et al |
| 5,916,449 | 06/29/1999 | Ellwart et al. |
| 6,589,792 | 07/08/2003 | Malachowski |
| 6,248,590 | 06/19/2001 | Malachowski |
| 4,361,400 | 11/30/1982 | Gray et al. |

II. FOREIGN PATENT DOCUMENTS

| Foreign Patent Document Country Code, Number, Kind Code (if known) | PUB'N DATE mm-dd-yyyy | PATENTEE OR APPLICANT NAME |
|---|---|---|
| DE19549015 | 03-04-97 | Ellwart et al. |
| EP 0781985 A2 | 07-02-97 | Karls et al. |
| EP0160201A2 | 11/06/85 | Sage et al. |
| EP025296A2 | 03/18/81 | Lombardo et al. |
| EP0468100A1 | 01/29/92 | Kosaka, Tokihiro |
| EP0786079 B1 | 05/21/2003 | Van Den Engh |
| FR2699678-A1 | 12/23/92 | MERLU BENOIT |
| JP 4-126066 | 04/27/92 | SAKAMOTO KAZUCHIKA, et al. |
| JP 4-126081 | 04/27/92 | SAKAMOTO KAZUCHIKA, et al. |
| JP2024535 | 01/26/90 | MIYAMOTO MORITOSHI, et al. |
| JP4126064 (A) | 04/27/92 | SHIOMI ATSUSHI, et al. |
| JP4126066 (A) | 04/27/92 | SAKAMOTO KAZUCHIKA, et al. |
| JP4126081 (A) | 04/27/92 | SAKAMOTO KAZUCHIKA et al. |
| JP61139747 (A) | 06/27/86 | ITO YUJI |
| JP61159135 (A) | 07/18/86 | ITO YUJI |
| SU1056008 | 11/23/83 | TRETYAKOV ALEKSANDR et al. |
| SU1260778-A1 | 09/30/86 | YAGUNOV ALEKSEJ et al |
| WO96/12172 A1 | 04/25/1996 | Van Den Engh |
| WO 99/44037 | 02/26/99 | Malachowski |
| WO01/28700 A1 | 04/26/2001 | Ellison, et al. |

III. OTHER DOCUMENTS

Axicon; Journal of the Optical Society of America; Vol. 44, #8, Eastman Kodak Company, Hawk-Eye Works, Rochester, NY, Sep. 10, 1953, pp. 592-597
Ceruzzi, P., "History of Modern Computing", MIT Press, Reference to Non-von Neumann.
Denk, W., et al (1995). Two-photon molecular excitation in laser scanning microscopy. Handbook of Biological Conical Microscopy. J. B. Pawley, ed., Plenum Press, New York, pp 444-458.
Garner, D. L. et al; "Quantification of the X- and Y- Chromosome-Bearing Spermatozoa of Domestic Animals by Flow Cytometry[1], Biology of Reproduction 28, pgs. 312-321, (1983)
Goppert-Mayer, M. 1931,. Über Elementarakte mit zwei Quantensprüngen
nnalen der Physik, Pages 273-294
Johnson, Lawrence A. "Sex Preselection by Flow Cytometric Separation of X and Y Chromosome-bearing Sperm based on NA Difference: a Review, Reprod. Fertil. Dev., 1995, 7, pgs. 893-903
Manni, Jeff; (1996). Two-Photon Excitation Expands The Capabilities of Laser-Scanning Microscopy, Biophotonics International, pp 44-52
Melamed et al, An Historical Review of the Development of Flow Cytometers and Sorters,, 1979, pp. 3-9
Piston. D. W.. et al (1994). Two-photon-excitation fluorescence imaging of three-dimensional calcium ion activity. APPLIED OPTICS 33: 662-669
Piston, D. W., et al. (1995). Three-dimensionally resolved NAD(P)H cellular metabolic redox imaging of the in-situ cornea with two-photon excitation laser scanning microscopy. J OF MICROSCOPY 178: 20-27

| III. OTHER DOCUMENTS |
|---|
| Radbruch, A Flow Cytometry and Cell Sorting,. (Ed.), "Operation of a Flow Cytometer" by Gottlinger et al., 1992, p. 7-23 |
| Sharpe, J., Thesis: "An Introduction to Flow Cytometry," pp 5-7 and pp 33-42 and page 55. |
| Shapiro, H. M.D., "Practical Flow Cytometry", Third Edition, John Wiley & Sons, Inc., Publication. |
| Skogen-Hagenson, M. J. et al; "A High Efficiency Flow Cytometer," The Journal of Histochemistry and Cytochemistry, Vol. 25, No. 7, pp. 784-789, 1977, USA |
| Van Dilla et al. (Eds.), Flow Cytometry: Instrumentation and Data Analysis, "Flow Chambers and Sample Handling," by Pinkel et al., 1985, pp. 77-128 |
| Van Dilla et al. (Eds.)Flow Cytometry: Instrumentation and Data Analysis,, "Overview of Flow Cytometry: Instrumentation and Data Analysis" by Martin Van Dilla, 1985, pp. 1-8 |
| Williams, R. M. et al. (1944). Two photon molecular excitation provides intrinsic 3-dimensional resolution for laser-based microscopy and microphotochemistry. FASEB J. 8: 804-813. |
| "An Introduction to Flow Cytometry", pp 5-7 and pp 33-42 and page 55. |
| Gottlinger, C., et al, "Operation of a Flow Cytometer," Flow Cytometry and Cell Sorting, pp. 7-23 (1982) |
| McLeod, J., Eastman Kodak Company, Hawk-Eye Works, Rochester, NY, Journal of the Optical Society of America; vol. 44, no. 8, September 1953, pp. 592-597 |
| Pinkel, D., "Flow Chambers and Sample Handling," Flow Cytometry: Instrumentation and Data Analysis, pp. 77-128 (1985) |
| U.S. application 09/032,733, entitled "Method and Apparatus for Flow Cytometry," filed on Feb. 27, 1998, 53 pages and 5 figures |
| U.S. application No. 60/591,957, entitled, "Geometric Transformation for Enhanced Flow Cytometry Discrimination," filed Jul. 7, 2004, 19 pages. |

Thus, the applicant(s) should be understood to have support to claim and make a statement of invention to at least: i) each of the transformation devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, xii) each potentially dependent claim or concept as a dependency on each and every one of the independent claims or concepts presented.

In addition and as to computer aspects and each aspect amenable to programming or other electronic automation, the applicant(s) should be understood to have support to claim and make a statement of invention to at least: xiii) processes performed with the aid of or on a computer as described throughout the above discussion, xiv) a programmable apparatus as described throughout the above discussion, xv) a computer readable memory encoded with data to direct a computer comprising means or elements which function as described throughout the above discussion, xvi) a computer configured as herein disclosed and described, xvii) individual or combined subroutines and programs as herein disclosed and described, xviii) the related methods disclosed and described, xix) similar, equivalent, and even implicit variations of each of these systems and methods, xx) those alternative designs which accomplish each of the functions shown as are disclosed and described, xxi) those alternative designs and methods which accomplish each of the functions shown as are implicit to accomplish that which is disclosed and described, xxii) each feature, component, and step shown as separate and independent inventions, and xxiii) the various combinations and permutations of each of the above.

With regard to claims whether now or later presented for examination, it should be understood that for practical reasons and so as to avoid great expansion of the examination burden, the applicant may at any time present only initial claims or perhaps only initial claims with only initial dependencies. Support should be understood to exist to the degree required under new matter laws—including but not limited to European Patent Convention Article 123(2) and United States Patent Law 35 U.S.C. §132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

We claim:

1. A method of operating a flow cytometry apparatus with at least n detectors to analyze at least two populations of particles in the same sample, the method comprising:
   (a) establishing a fluid stream in the flow cytometry apparatus with at least n detectors, the at least n detectors including a first detector and a second detector;
   (b) entraining particles from the sample in the fluid stream in the flow cytometry apparatus;
   (c) executing instructions read from a computer readable memory with a processor, the processor being in communication with the first detector in the flow cytometer, to detect a first signal from the first detector based on individual particles in the fluid stream;
   (d) executing instructions read from the computer readable memory with the processor, the processor being in communication with the second detector in the flow cytometer, to detect a second signal from the second detector based on the individual particles in the fluid stream;
   (e) executing instructions read from the computer readable memory with the processor to convert at least the first signal and the second signal into n-dimensional parameter data for detected particles in the sample, wherein the n-dimensional parameter data for particles from the at least two populations overlap in at least one of the dimensions;
   (f) executing instructions read from the computer readable memory with the processor to rotationally alter the n-dimensional parameter data so that spatial separation of the data from the particles from the at least two populations in the at least one dimension that is overlapped is increased;
   (g) executing instructions read from the computer readable memory with the processor to real-time classify each of the individual detected particles into one of a first population and a second population of the at least two populations based on at least the rotationally altered n-dimensional parameter data; and
   (h) using the real-time classification, sorting the individual particles with the flow cytometer.

2. The method of claim 1, further comprising:
   (a) executing instructions with the processor read from the computer readable memory to create a first dimensional altered data point by calculating a first 1st-dimensional alteration value times a 1 st-dimensional data point summed with a second 1 st-dimensional alteration value times a 2nd-dimensional data point summed with a third 1 st-dimensional alteration value times a 3rd-dimensional data point; and
   (b) executing instructions with the processor read from the computer readable memory to create a second dimensional altered data point by calculating a first 2nd-dimensional alteration value times the 1 st-dimensional data point summed with a second 2nd-dimensional alteration value times the 2nd-dimensional data point summed with a third 2nd-dimensional alteration value times the 3rd-dimensional data point.

3. The method of claim 1, wherein the rotational alteration increases discrimination between the first population and the second population.

4. The method of claim 1, further comprising:
   (a) altering the n-dimensional parameter data by scaling the n-dimensional parameter data; and
   (b) real-time classifying the n-dimensional parameter data of each of the individual particles into one of the at least two populations based on at least the scaled n-dimensional parameter data.

5. The method of claim 4, further comprising
   (a) executing instructions with the processor read from the computer readable memory to create a first dimensional altered data point by calculating a first 1st-dimensional alteration value times a 1 st-dimensional data point summed with a second 1 st-dimensional alteration value times a 2nd-dimensional data point summed with a third 1 st-dimensional alteration value times a 3rd-dimensional data point; and
   (b) executing instructions read from the computer readable memory with the processor to create a second dimensional altered data point by calculating a first 2nd-dimensional alteration value times the 1 st-dimensional data point summed with a second 2nd-dimensional alteration value times the 2nd-dimensional data point summed with a third 2nd-dimensional alteration value times the 3rd-dimensional data point.

6. The method of claim 5, wherein the alteration values are based on a zoom and tracking element and the alteration increases discrimination between the first population and the second population in the n-dimensional parameter data.

7. The method of claim 4, further comprising:
   executing instructions read from the computer readable memory with the processor to simultaneously rotationally alter and scale the n-dimensional parameter data.

8. The method of claim 1 or 4, further comprising:
   (a) executing instructions read from the computer readable memory with the processor to alter the n-dimensional parameter data by translating the n-dimensional parameter data; and
   (b) executing instructions read from the computer readable memory with the processor to real-time classify each of the individual particles into one of said the first population and the second population based on at least the translated n-dimensional parameter data.

9. The method of claim 8, further comprising:
   (a) executing instructions read from the computer readable memory with the processor to create a first dimensional altered data point by calculating a first 1st-dimensional alteration value times a 1 st-dimensional data point summed with a second 1 st-dimensional alteration value times a 2nd-dimensional data point summed with a third 1 st-dimensional alteration value times a 3rd-dimensional data point; and
   (b) executing instructions read from the computer readable memory with the processor to create a second dimensional altered data point by calculating a first 2nd-dimensional alteration value times the 1 st-dimensional data point summed with a second 2nd-dimensional alteration value times the 2nd-dimensional data point summed with a third 2nd-dimensional alteration value times the 3rd-dimensional data point.

10. The method of claim 9, wherein the alteration values comprise translating of the n-dimensional parameter data with respect to a center point of rotation.

11. The method of claim 9, wherein the alteration values are based on an operation selected from a group consisting of rotation in x-axis, rotation in y-axis, rotation in z-axis, translation, scale, and perspective operations.

12. The method of claim 8, further comprising:
executing instructions read from the computer readable memory with the processor to simultaneously rotationally alter, scale, and translate the n-dimensional parameter data.

13. The method of claim 1, further comprising:
executing instructions read from the computer readable memory with the processor to cause a display device to display the n-dimensional parameter data for each of the individual particles in relation to the at least two populations.

14. The method of claim 1, further comprising:
executing instructions read from the computer readable memory with the processor to cause a display device to display the n-dimensional parameter data in a Cartesian coordinate system.

15. The method of claim 14, further comprising:
executing instructions read from the computer readable memory with the processor to cause the display device to display:
(a) the first signal on a first axis; and
(b) the second signal on a second axis.

16. The method of claim 1, further comprising:
executing instructions read from the computer readable memory with the processor to cause a display device to display a histogram of the n-dimensional parameter data.

17. The method of claim 1, further comprising:
executing instructions read from the computer readable memory with the processor to cause a display device to display:
(a) elliptical shaped populations of each of the first population and the second population, the displayed elliptical shaped populations having non-orthogonal angles of inclination to at least one axis; and
(b) the elliptical shaped populations orthogonal to at least one axis.

18. The method of claim 1, wherein:
(a) the particles include sperm; and
(b) the first population includes an X-bearing sperm population; and
(c) the second population includes a Y-bearing sperm population.

19. The method of claim 1, wherein the first signal and the second signal comprises fluorescence emitted from a light emitting element coupled with the individual particles after passing through a laser beam.

20. The method of claim 1, further comprising:
identifying a point situated between the first population and second population when the n-dimensional parameter data for a first plurality of particles from the first population and a second plurality of particles from the second population is plotted on a Cartesian coordinate system, such that the point is positioned so that the separation of the first population and second population is increased with respect to one axis of the Cartesian coordinate system when the n-dimensional parameter data for the first and second plurality of particles is rotated about the point, and
wherein rotationally altering the n-dimensional parameter data includes rotating the n-dimensional parameter data about the point.

21. The method of claim 1, wherein the processor is a digital signal processor.

22. The method of claim 21, wherein the digital signal processor is a fixed point processor.

23. The method of claim 1 wherein the instructions are assembly language code.

* * * * *